(12) United States Patent
Weigand et al.

(10) Patent No.: US 11,965,102 B2
(45) Date of Patent: Apr. 23, 2024

(54) PHOTOCHROMIC ANNELATED NAPHTHOPYRANE SYSTEMS WITH SPECIAL SUBSTITUENTS, FOR ATTAINING RAPID LIGHTENING SPEEDS

(71) Applicant: RODENSTOCK GMBH, Munich (DE)

(72) Inventors: Udo Weigand, Munich (DE); Herbert Zinner, Rohrbach (DE); Yven Rohlfing, Munich (DE)

(73) Assignee: RODENSTOCK GMBH (DE)

( * ) Notice: Subject to any disclaimer, the term of this patent is extended or adjusted under 35 U.S.C. 154(b) by 675 days.

(21) Appl. No.: 17/251,445

(22) PCT Filed: Jun. 5, 2019

(86) PCT No.: PCT/EP2019/064652
§ 371 (c)(1),
(2) Date: Dec. 11, 2020

(87) PCT Pub. No.: WO2019/238495
PCT Pub. Date: Dec. 19, 2019

(65) Prior Publication Data
US 2021/0253865 A1 Aug. 19, 2021

(30) Foreign Application Priority Data
Jun. 14, 2018 (DE) ...................... 10 2018 004 790.4

(51) Int. Cl.
*C09K 9/02* (2006.01)
*C09B 69/10* (2006.01)
*G02C 7/10* (2006.01)

(52) U.S. Cl.
CPC .............. *C09B 69/109* (2013.01); *C09K 9/02* (2013.01); *C09K 2211/1018* (2013.01); *G02C 7/102* (2013.01)

(58) Field of Classification Search
CPC . C09B 69/109; C09K 9/02; C09K 2211/1018; G02C 7/102
See application file for complete search history.

(56) References Cited

U.S. PATENT DOCUMENTS

| 3,567,605 | A | 3/1971 | Becker |
| 6,291,561 | B1 | 9/2001 | Breyne et al. |
| 2016/0152629 | A1* | 6/2016 | Weigand ................ G02C 7/022 428/411.1 |

FOREIGN PATENT DOCUMENTS

| EP | 0792468 A1 | 9/1997 |
| EP | 0906366 A1 | 4/1999 |
| EP | 0912908 A1 | 5/1999 |
| EP | 0946536 A1 | 10/1999 |
| EP | 1038870 | 9/2000 |
| EP | 1097156 A2 | 5/2001 |
| EP | 1112264 A1 | 7/2001 |
| EP | 1119560 A1 | 8/2001 |
| EP | 2178883 A1 | 4/2010 |

(Continued)

OTHER PUBLICATIONS

English Translation of International Search Report dated Sep. 11, 2019; International Patent Application No. PCT/EP2019/064652 filed Jun. 5, 2019. ISA/EP.

*Primary Examiner* — Marcos L Sznaidman
(74) *Attorney, Agent, or Firm* — McDonald Hopkins LLC

(57) ABSTRACT

The present invention relates to new photochromic, fused naphthopyran systems having specific substituents $R_1$, which can be used to attain very rapid lightening speeds, without detriment to the depth of darkening after excitation, and also to the use thereof in plastics of all kinds.

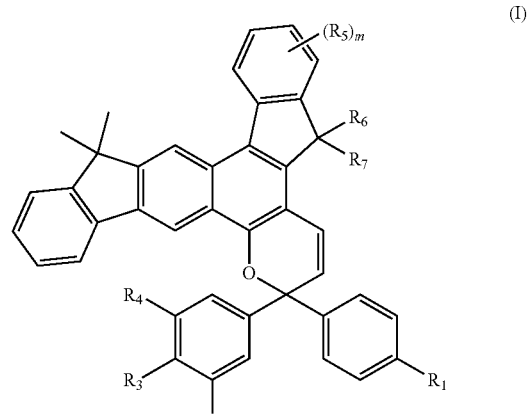

(I)

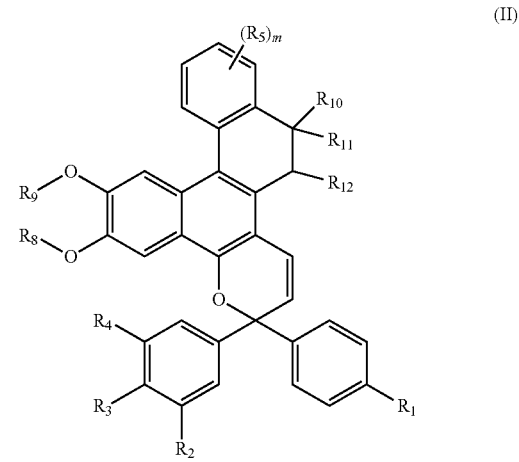

(II)

5 Claims, No Drawings

(56) References Cited

FOREIGN PATENT DOCUMENTS

| EP | 2457915 A1 | 5/2012 |
|---|---|---|
| EP | 2471794 A1 | 7/2012 |
| EP | 2684886 A1 | 1/2014 |
| EP | 2760869 A1 | 8/2014 |
| EP | 2788340 A1 | 10/2014 |
| EP | 2829537 A1 | 1/2015 |
| EP | 2872517 A1 | 5/2015 |
| EP | 3010924 A1 | 4/2016 |
| RU | 2175321 | 12/2000 |
| RU | 99106203 | 1/2001 |

* cited by examiner

PHOTOCHROMIC ANNELATED NAPHTHOPYRANE SYSTEMS WITH SPECIAL SUBSTITUENTS, FOR ATTAINING RAPID LIGHTENING SPEEDS

The present invention relates to new photochromic, fused naphthopyran systems having specific substituents $R_1$, which can be used to attain very rapid lightening speeds, without detriment to the depth of darkening after excitation, and also to the use thereof in plastics of all kinds.

For a long time there have been various classes of dye known which change their color reversibly on irradiation with UVA light, especially the rays of the sun. The underlying reason for this is that light energy causes these dye molecules to transition to an excited state ("open form") which they depart again when the supply of energy is interrupted, reverting to their original state ("closed form"). Among these photo-chromic dyes are various systems having core pyran structures, which have already been described in the prior art with various parent systems and substituents.

Pyrans, specifically naphthopyrans and larger ring systems derived from them, are currently the most widely engaged class of photochromic compounds. Although the first patent was filed back in 1966 (U.S. Pat. No. 3,567,605), it was not until the 1990s that compounds were able to be developed which appeared suitable for use in eyewear lenses. A suitable class of pyran compounds are, for example, the 2,2-diaryl-2H-naphtho[1,2-b]pyrans or the 3,3-diaryl-3H-naphtho[2,1-b]pyrans, which in excited form have different darkening colors from yellow to red.

Deriving from these parent systems, there is great interest in fused naphthopyrans, which by virtue of their sizeable ring system absorb at longer wavelengths and produce violet and blue darkening colors. Employed typically for these purposes is a benzene ring having additional bridging in the ortho-position—in the compounds of the invention presented here, the bridge with the substituents $R_6$ and $R_7$ for compounds of the formula (I) or with the substituents $R_{10}$, $R_{11}$ and $R_{12}$ for compounds of the formula (II).

Where there is a single-atom bridge, as in the case of the compounds of the formula (I) of the invention, the result is a five-membered ring fused to the naphthopyran. Examples are found in EP 0 792 468 and EP 0 906 366 for a carbon bridge atom ("indenonaphthopyrans") and also in EP 0 946 536 for an oxygen bridge atom.

EP0912908, EP2457915, EP2471 794, EP2684886, EP2788340 and EP 2 872 517 describe compounds comprising at least one further ring system fused to the core indenonaphthopyran structure.

Where there is a two-atom bridge, as in the case of the compounds of formula (II) of the invention, the result is a six-membered ring fused to the naphthopyran. Compounds having a bridge composed of two carbon atoms are described in EP 1 119 560. More recent relevant applications are EP 2 829 537 and also EP 3 010 924.

EP 1 097 156 describes compounds having a two-atom bridge composed of one carbon and one oxygen atom, as do EP 2 178 883 and EP 2 760 869. Systems described in EP 1 112 264 include indenonaphthopyran systems (with no further fusions) having relatively long polyalkoxy substituents.

It is an object of the present invention, therefore, to provide photochromic dyes which are to be distinguished by very rapid lightening speeds, without detriment to the depth of darkening after excitation.

This object is achieved by the subjects characterized in the claims.

Provided more particularly are photochromic fused naphthopyrans of the general formulae (I) and (II):

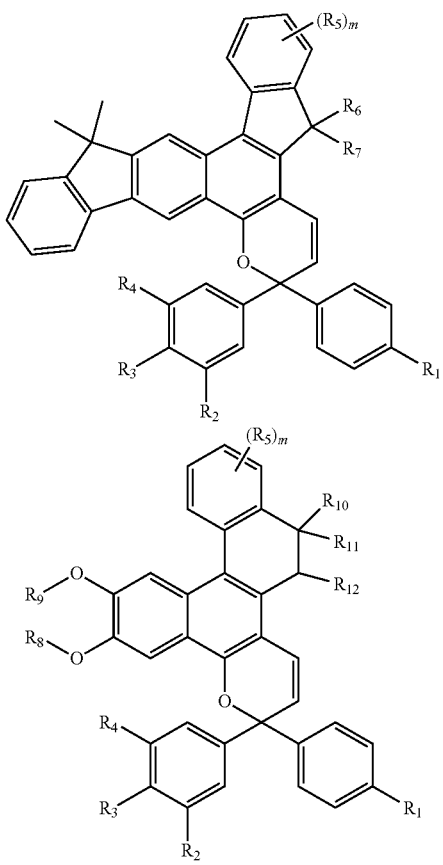

in which either only the radical $R_1$ or both $R_1$ and $R_3$ independently of one another represents or represent the following moiety:

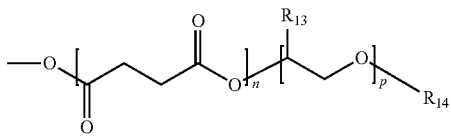

in which the radical $R_{13}$ is hydrogen or a methyl radical and the radical $R_{14}$ is a substituent selected from hydrogen, a $(C_1\text{-}C_6)$-alkyl radical, an acetyl radical, a benzoyl radical, a phenyl radical, a benzyl radical, a biphenylyl radical, a naphthyl radical, a tert-butyldimethylsilyl radical or a tert-butyldiphenylsilyl radical; n is an integer from 0 to 1, and p is an integer from 3 to 50;

or, if $R_{13}$ is a methyl radical, $R_{14}$ may also be the moiety $-(CH_2-CH_2)_q-OR_{15}$, in which case the radical $R_{15}$ may be selected from hydrogen, a $(C_1\text{-}C_8)$-alkyl radical, a phenyl radical, a benzyl radical or a biphenylyl radical, and q is an integer from 1 to 20; and the radicals $R_2$, $R_3$ and $R_4$ in each case independently of one another are a substituent selected from hydrogen, bromine, chlorine, fluorine, a $(C_1\text{-}C_6)$-alkyl radical, a $(C_3\text{-}C_7)$— cycloalkyl radical, a $(C_1\text{-}C_6)$-thioalkyl radical, a $(C_1\text{-}C_{18})$-alkoxy radical, a hydroxyl radical, a tert-butyldimethylsilyloxy radical, a tert-butyldiphenylsilyloxy radical, a trifluoromethyl radical, a phenyl radical, a 4-methoxyphenyl radical, a phenoxy radical, a 4-methoxyphenoxy radical, a benzyl radical, a 4-methoxybenzyl radical, a benzyloxy radical, a 4-methoxybenzyloxy radical, a biphenylyl radical, a diphenylyloxy radical, a naphthyl radical, a naphthoxy radical, a mono-$(C_1$-$C_6)$-alkylamino radical, a di-$(C_1$-$C_6)$-alkylamino radical, a phenylamino radical, a $(C_1$-$C_6)$-alkyl-phenylamino radical, a diphenylamino radical, a (4-methoxyphenyl)amino radical, a (($(C_1$-$C_6)$-alkyl)-(4-methoxyphenyl)amino radical, a bis(4-methoxyphenyl)amino radical, a piperidyl radical, a 3,5-dimethylpiperidyl radical, an indolinyl radical, a morpholinyl radical, a 2,6-dimethylmorpholinyl radical, a thiomorpholinyl radical, an azacycloheptyl radical, a phenothiazinyl radical, a phenoxazinyl radical, a 1,2,3,4-tetrahydroquinolyl radical, a 1,2,3,4-tetrahydroisoquinolyl radical, a phenazinyl radical, a carbazolyl radical, a 1,2,3,4-tetrahydrocarbazolyl radical or a 10,11-dihydrodibenz[b,f]azepinyl radical;

or the two adjacent radicals $R_2$ and $R_3$ are the moiety —V—$(CH_2)_r$—W—, in which case V and W independently of one another are selected from the moieties —O—, —S—, —N$(C_1$-$C_6)$-alkyl-, —N$C_6H_5$—, —$CH_2$—, —$C(CH_3)_2$—, —$C(C_2H_5)_2$— or —$C(C_6H_5)_2$—; r is an integer from 1 to 3; with the proviso that if this numerical value is 2 or 3, there may also be a benzene ring fused to two adjacent $CH_2$ groups; V or W, together with the respectively adjacent $CH_2$ group, may also be a fused benzene ring;

or, as already defined above, $R_3$ is the same moiety as $R_1$;

the radicals $R_5$, $R_6$, $R_7$, $R_8$, $R_9$, $R_{10}$, $R_{11}$ and $R_{12}$ each independently of one another are a substituent selected from hydrogen, a $(C_1$-$C_6)$-alkyl radical, a $(C_3$-$C_6)$-cycloalkyl radical, a phenyl radical, a benzyl radical, a biphenylyl radical or a naphthyl radical; where m is an integer from 1 to 3;

or two adjacent radicals $R_5$ form a fused benzene ring, which may be unsubstituted or mono- or disubstituted, in which case the substituents may be selected from hydrogen, a $(C_1$-$C_6)$-alkyl radical, a $(C_1$-$C_6)$-alkoxy radical, a phenyl radical, a benzyl radical, a biphenylyl radical or a naphthyl radical;

or two adjacent radicals $R_5$ form a fused benzofuran ring, a fused benzothiophene ring, a fused 2H-chromene ring, a fused 3,3-dimethylindene ring or a fused dioxane ring; or the radicals $R_6$ and $R_7$, together with the carbon atom bonded to these radicals, form a three- to eight-membered carbo- or heteromonocyclic ring to which one to two aromatic or heteroaromatic ring systems may be fused, in which case the ring system or systems independently of one another are selected from benzene, naphthalene, phenanthrene, pyridine, quinoline, furan, thiophene, pyrrole, benzofuran, benzothiophene, indole and carbazole;

or the radicals $R_8$ and $R_9$ together form the moiety —$(CH_2)_s$—, in which case s is an integer from 1 to 3; with the proviso that if this numerical value is 2 or 3, there may also be a benzene ring fused to two adjacent $CH_2$ groups.

The present invention is based on the surprising finding that through the introduction of specific substituents $R_1$ into photochromic dye systems from the prior art—from EP 2 788 340 for compounds of formula (I) and from EP 3 010 924 for compounds of formula (II), respectively—it is possible to attain very rapid lightening speeds without detriment to the depth of darkening after excitation.

The specific substituents $R_1$ are relatively long linear polyethyleneoxy and/or polypropyleneoxy chains, which are covalently bonded optionally via a succinyl ester bridge to the photochromic dye. With their long chainlike structure, these substituents apparently shield the dye molecules from the plastics matrix so effectively that they create an environment which is independent of the polarity and the chemistry of the plastics matrix and which provides less stabilization to the excited, colored (open) form of the dyes. As a result, after excitation, the photochromic dye molecules revert more rapidly to their colorless ground state, meaning that the dye lightens more quickly after excitation. The long chainlike structures of the specific substituents $R_1$ wrap around the dye molecules to construct, so to speak, a protective wall which shields the dyes from the plastics matrix. Reasons why the substituents $R_1$ are particularly efficient is that they lie close to the photolabile center of the photochromic dye and hence close to the location where the bond is broken on excitation and reformed on lightening, respectively. The polarity of the chains of $R_1$ is a decisive factor—for example, long paraffin chains do not exhibit any effect at all.

A distinguishing feature of the compounds of the invention is that through the introduction of specific substituents $R_1$ into photochromic dye systems from the prior art—from EP 2 788 340 for compounds of formula (I) and from EP 3 010 924 for compounds of formula (II)—significantly improved lightening properties can be induced. Hence the phototropic properties of these dye systems can be significantly improved, since the depth of darkening is unaffected by the introduction of the substituents $R_1$. Like the parent systems without the substituents $R_1$, the compounds of the invention are notable for their outstanding compatibility with UV curing, since when incorporated, for example, into an acrylate monomer matrix with UV initiator, they withstand intact a radical polymerization of the matrix that is initiated by strong UV light. They also combine very high performance with a very long life. They can be deployed in plastics of all kinds.

The molecular structure of the compounds of the invention is based on a core indeno-naphthopyran structure (with the substituents $R_5$, $R_6$ and $R_7$) for compounds of the formula (I) or core dihydronaphtho-naphthopyran structure (with the substituents $R_5$, $R_8$, $R_9$, $R_{10}$, $R_{11}$ and $R_{12}$) for compounds of the formula (II), each containing the photolabile pyran unit (with the substituents $R_1$, $R_2$, $R_3$ and $R_4$). This is responsible for the photochromic character, since excitation by light causes reversible breaking of the bond between the oxygen in the pyran unit and the carbon atom with the two aryl substituents, so creating a colored merocyanine system.

The compounds of the invention are synthesized according to FIG. 3 from the parent dye systems from the prior art having a hydroxyl group in the place of $R_1$.

For measuring the spectral and photochromic properties, equimolar amounts of the compounds of the invention and of compounds from the prior art were dissolved in an acrylate monomer matrix and subjected, following the addition of a polymerization initiator, to thermal polymerization with the aid of a temperature program.

The photochromic darkening and lightening behavior ("kinetic diagram") of the specimens thus produced was then determined according to DIN EN ISO 8980-3.

FIG. 1 shows the kinetic comparison of compounds of the general formula (I) of the invention, more specifically having the formula (III) below, with corresponding compounds from the prior art from EP 2 788 340.

FIG. 2 shows the kinetic comparison of compounds of the general formula (II) of the invention, more specifically having the formula (IV) below, with corresponding compounds from the prior art from EP 3 010 924.

The specific molecular structures of the compounds shown in FIGS. 1 and 2 are set out in table 1. The compounds 1 and 2 of the invention are described in table 1 below by the formula (III), compounds 3 and 4 of the invention by the formula (IV).

FIGS. 1 and 2 show illustratively the clear effect of the specific substituents $R_1$ of the invention on the lightening speed, without detriment to the depth of darkening.

The compounds 1 and 3 of the invention have a linear polyethyleneoxy chain in the substituent $R_1$, with an average chain length of about 16. Starting material for the synthesis is commercially available polyethylene glycol monomethyl ether having an average molecular weight of 750. Here there is a Gaussian distribution of different chain lengths, with a maximum at about 16 ethyleneoxy units.

The compounds 2 and 4 of the invention have a linear polypropyleneoxy chain in the substituent $R_1$, with an average chain length of about 17. Starting material for the synthesis is commercially available polypropylene glycol having an average molecular weight of 1000. Here again

TABLE 1

Molecular structures of the compounds presented in figures 1 and 2

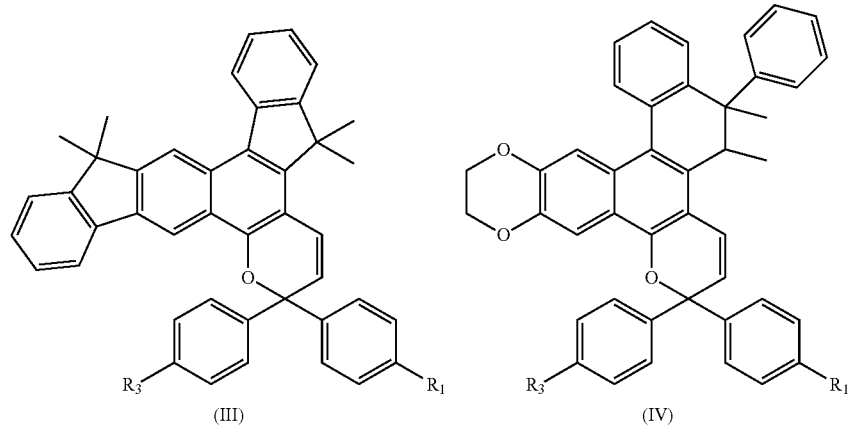

(III)                                   (IV)

| | $R_1$ in formula (III) | $R_3$ in (III) | $R_1$ in formula (IV) | $R_3$ in (IV) |
|---|---|---|---|---|
| Compound 1 from prior art (EP 2 788 340) | OMe (= methoxy) | OMe | | |
| Compound 1 of the invention | ![structure] Me = methyl; p = 16 (Gaussian distribution) | OMe | | |
| Compound 2 of the invention | ![structure] Et = ethyl; p = 17 | OMe | | |
| Compound 2 from prior art (EP 3 010 924) | | | OMe | Me (= methyl) |
| Compound 3 of the invention | | | ![structure] Me = methyl; p = 16 (Gaussian distribution) | Me |
| Compound 4 of the invention | | | ![structure] Et = ethyl; p = 17 | Me | there is a Gaussian distribution of different chain lengths, with a maximum at about 17 propyleneoxy units. The 2-ethoxyethyl end group is introduced by means of a conventional Williamson ether synthesis using 2-bromoethyl ethyl ether.

The effect of the acceleration of the lightening speed is observable not only for the chain lengths described above; shorter chains with fewer than 10 units likewise display the effect.

According to the synthesis scheme in FIG. 3, the compounds of the invention are then prepared from these. The method is the same for both types of formula—in FIG. 3, therefore, only the pyran ring with the two aryl substituents is shown (n refers to the formula of the substituent $R_1$ in claim 1). If n is 1, the aforementioned longer-chain starting compounds are attached covalently to the photochromic dye molecule by means of an ester synthesis. The carboxyl group in the succinyl unit is activated using CDI (carbonyldiimidazole), which permits a very mild ester synthesis. If n is 0, the longer-chain starting compound must first be activated in the form of tosylate (Ts). This is followed by the covalent attachment to the photochromic dye molecule by means of a conventional Williamson ether synthesis.

Where the compounds of the invention are employed in plastics of all kinds, the photochromic properties can be improved further by means of additives. Preferred additives are compounds constructed from the same structural units as substituent $R_1$ and therefore able to configure the chemical environment of the photolabile dye molecules in a similar way to substituent $R_1$, but they are not fixed in a diffusion-stable way. Preferred examples are therefore linear polyethylene glycols of various chain lengths, linear polypropylene glycols of various chains lengths, oligomers constructed in alternation of ethyleneoxy and propyleneoxy units, and also block copolymers composed of ethyleneoxy and propyleneoxy units. End groups used, other than hydroxyl groups, may also be alkyl radicals or other groups.

A further subject of the present invention concerns the use of one or more of the photochromic fused naphthopyran systems of the invention in plastics of all kinds, more particularly for ophthalmic purposes, in optical lenses and lenses for eyewear of all kinds, such as, for example, corrective spectacles, driver's glasses, ski goggles, sunglasses, motorcycle goggles, for visors of protective helmets and the like, and for sun protection in vehicles and in the architectural sector, in the form of windows, protective shades, covers, roofs and the like. In the case of use in plastics of all kinds, adjuvants of all kinds may be used together with the compounds of the invention. Preference, as already set out above, is given to linear polyethylene glycols, linear polypropylene glycols, oligomers composed in alternation of ethyleneoxy and propyleneoxy units, and also block copolymers composed of ethyleneoxy and propyleneoxy units. End groups of the oligomer additives, other than hydroxyl groups, may also be alkyl groups or other groups.

The invention claimed is:
1. Photochromic fused naphthopyrans of the formula (II):

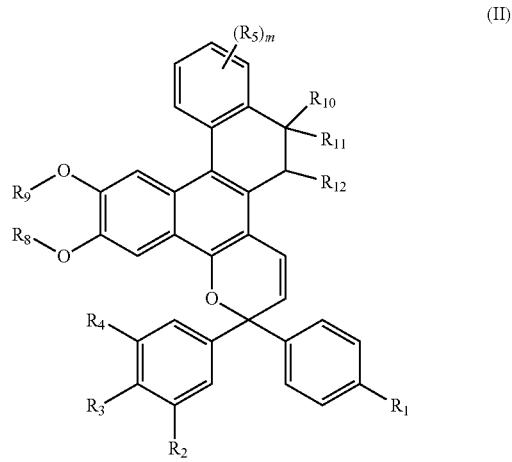

in which the radical $R_1$, or $R_1$ and $R_3$ independently of one another, is/are the following moiety:

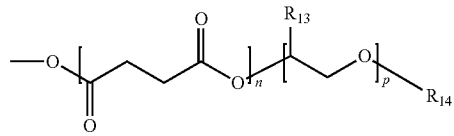

in which the radical $R_{13}$ is hydrogen or a methyl radical and the radical $R_{14}$ is a substituent selected from hydrogen, a ($C_1$-$C_6$)-alkyl radical, an acetyl radical, a benzoyl radical, a phenyl radical, a benzyl radical, a biphenylyl radical, a naphthyl radical, a tert-butyldimethylsilyl radical or a tert-butyldiphenylsilyl radical; n is an integer from 0 to 1, and p is an integer from 3 to 50; or, if $R_{13}$ is a methyl radical, $R_{14}$ may also be the moiety —($CH_2$—$CH_2$)$_q$—$OR_{15}$, in which case the radical $R_{15}$ may be selected from hydrogen, a ($C_1$-$C_6$)-alkyl radical, a phenyl radical, a benzyl radical or a biphenylyl radical, and q is an integer from 1 to 20; and the radicals $R_2$, $R_3$ and $R_4$ in each case independently of one another are a substituent selected from hydrogen, bromine, chlorine, fluorine, a ($C_1$-$C_6$)-alkyl radical, a ($C_3$-$C_7$)-cycloalkyl radical, a ($C_1$-$C_6$)-thioalkyl radical, a ($C_1$-$C_{18}$)-alkoxy radical, a hydroxyl radical, a tert-butyldimethylsilyloxy radical, a tert-butyldiphenylsilyloxy radical, a trifluoromethyl radical, a phenyl radical, a 4-methoxyphenyl radical, a phenoxy radical, a 4-methoxyphenoxy radical, a benzyl radical, a 4-methoxybenzyl radical, a benzyloxy radical, a 4-methoxybenzyloxy radical, a biphenylyl radical, a diphenylyloxy radical, a naphthyl radical, a naphthoxy radical, a mono-($C_1$-$C_6$)-alkylamino radical, a di-($C_1$-$C_6$)-alkylamino radical, a phenylamino radical, a ($C_1$-$C_6$)-alkyl-phenylamino radical, a diphenylamino radical, a (4-methoxyphenyl)amino radical, a (($C_1$-$C_6$)-alkyl)-(4-methoxyphenyl)amino radical, a bis(4-methoxyphenyl)amino radical, a piperidyl radical, a 3,5-dimethylpiperidyl radical, an indolinyl radical, a morpholinyl radical, a 2,6-dimethylmorpholinyl radical, a thiomorpholinyl radical, an azacycloheptyl radical, a phenothiazinyl radical, a phenoxazinyl radical, a 1,2,3,4-tetrahydroquinolyl radical, a 1,2,3,4-tetrahydroisoquinolyl radical, a phenazinyl radical, a carbazolyl radical, a 1,2,3,4-tetrahydrocarbazolyl radical or a 10,11-dihydrodibenz[b,f]azepinyl radical;

or the two adjacent radicals $R_2$ and $R_3$ are the moiety —V—$(CH_2)_r$—W—, in which case V and W independently of one another are selected from the moieties —O—, —S—, —N($C_1$-$C_6$)-alkyl-, —$NC_6H_5$—, —$CH_2$—, —$C(CH_3)_2$—, —$C(C_2H_5)_2$— or —$C(C_6H_5)_2$—; r is an integer from 1 to 3; with the proviso that if this numerical value is 2 or 3, there may also be a benzene ring fused to two adjacent $CH_2$ groups; V or W, together with the respectively adjacent $CH_2$ group, may also be a fused benzene ring;

or $R_3$ is the same moiety as $R_1$;

the radicals $R_5$, $R_8$, $R_9$, $R_{10}$, $R_{11}$ and $R_{12}$ each independently of one another are a substituent selected from hydrogen, a ($C_1$-$C_6$)-alkyl radical, a ($C_3$-$C_7$)-cycloalkyl radical, a phenyl radical, a benzyl radical, a biphenylyl radical or a naphthyl radical; where m is an integer from 1 to 3;

or two adjacent radicals $R_5$ form a fused benzene ring, which may be unsubstituted or mono- or disubstituted, in which case the substituents may be selected from hydrogen, a ($C_1$-$C_6$)-alkyl radical, a ($C_1$-$C_6$)-alkoxy radical, a phenyl radical, a benzyl radical, a biphenylyl radical or a naphthyl radical;

or two adjacent radicals $R_5$ form a fused benzofuran ring, a fused benzothiophene ring, a fused 2H-chromene ring, a fused 3,3-dimethylindene ring or a fused dioxane ring;

or the radicals $R_8$ and $R_9$ together form the moiety —$(CH_2)_s$—, in which case s is an integer from 1 to 3; with the proviso that if this numerical value is 2 or 3, there may also be a benzene ring fused to two adjacent $CH_2$ groups.

2. Photochromic fused naphthopyrans as claimed in claim 1, in which the radical $R_1$ represents the moiety:

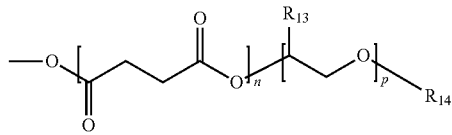

and the radical $R_3$ is a substituent selected from hydrogen, bromine, chlorine, fluorine, a ($C_1$-$C_6$)-alkyl radical, a ($C_3$-$C_7$)-cycloalkyl radical, a ($C_1$-$C_6$)-thioalkyl radical, a ($C_1$-$C_{18}$)-alkoxy radical, a hydroxyl radical, a tert-butyldimethylsilyloxy radical, a tert-butyldiphenylsilyloxy radical, a trifluoromethyl radical, a phenyl radical, a 4-methoxyphenyl radical, a phenoxy radical, a 4-methoxyphenoxy radical, a benzyl radical, a 4-methoxybenzyl radical, a benzyloxy radical, a 4-methoxybenzyloxy radical, a biphenylyl radical, a diphenylyloxy radical, a naphthyl radical, a naphthoxy radical, a mono-($C_1$-$C_6$)-alkylamino radical, a di-($C_1$-$C_6$)-alkylamino radical, a phenylamino radical, a ($C_1$-$C_6$)-alkyl-phenylamino radical, a diphenylamino radical, a (4-methoxyphenyl)amino radical, a (($C_1$-$C_6$)-alkyl)-(4-methoxyphenyl)amino radical, a bis(4-methoxyphenyl)amino radical, a piperidyl radical, a 3,5-dimethylpiperidyl radical, an indolinyl radical, a morpholinyl radical, a 2,6-dimethylmorpholinyl radical, a thiomorpholinyl radical, an azacycloheptyl radical, a phenothiazinyl radical, a phenoxazinyl radical, a 1,2,3,4-tetrahydroquinolyl radical, a 1,2,3,4-tetrahydroisoquinolyl radical, a phenazinyl radical, a carbazolyl radical, a 1,2,3,4-tetrahydrocarbazolyl radical or a 10,11-dihydrodibenz[b,f]azepinyl radical; and in which the other radicals are as defined above.

3. Photochromic fused naphthopyrans as claimed in claim 1, in which the radicals $R_5$, $R_8$, $R_9$, $R_{10}$, $R_{11}$ and $R_{12}$ each independently of one another are a substituent selected from hydrogen, a ($C_1$-$C_6$)-alkyl radical, a ($C_3$-$C_7$)-cycloalkyl radical, a phenyl radical, a benzyl radical, a biphenylyl radical or a naphthyl radical; where m is an integer from 1 to 3.

4. Photochromic fused naphthopyrans as claimed in claim 1, in which the radical $R_1$ represents the following moiety:

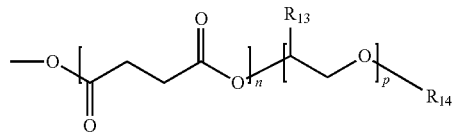

in which the radical $R_{13}$ is hydrogen or a methyl radical and the radical $R_{14}$ is a substituent selected from hydrogen, a ($C_1$-$C_6$)-alkyl radical, an acetyl radical, a benzoyl radical, a phenyl radical, a benzyl radical, a biphenylyl radical, a naphthyl radical, a tert-butyldimethylsilyl radical or a tert-butyldiphenylsilyl radical; n is an integer from 0 to 1, and p is an integer from 3 to 50; or, if $R_{13}$ is a methyl radical, $R_{14}$ may also be the moiety —$(CH_2$—$CH_2)_q$—$OR_{15}$, in which case the radical $R_{15}$ may be selected from hydrogen, a ($C_1$-$C_6$)-alkyl radical, a phenyl radical, a benzyl radical or a biphenylyl radical, and q is an integer from 1 to 20; and the radical $R_3$ is a substituent selected from hydrogen, bromine, chlorine, fluorine, a ($C_1$-$C_6$)-alkyl radical, a ($C_3$-$C_7$)-cycloalkyl radical, a ($C_1$-$C_6$)-thioalkyl radical, a ($C_1$-$C_{18}$)-alkoxy radical, a hydroxyl radical, a tert-butyldimethylsilyloxy radical, a tert-butyldiphenylsilyloxy radical, a trifluoromethyl radical, a phenyl radical, a 4-methoxyphenyl radical, a phenoxy radical, a 4-methoxyphenoxy radical, a benzyl radical, a 4-methoxybenzyl radical, a benzyloxy radical, a 4-methoxybenzyloxy radical, a biphenylyl radical, a diphenylyloxy radical, a naphthyl radical, a naphthoxy radical, a mono-($C_1$-$C_6$)-alkylamino radical, a di-($C_1$-$C_6$)-alkylamino radical, a phenylamino radical, a ($C_1$-$C_6$)-alkyl-phenylamino radical, a diphenylamino radical, a (4-methoxyphenyl)amino radical, a (($C_1$-$C_6$)-alkyl)-(4-methoxyphenyl)amino radical, a bis(4-methoxyphenyl)amino radical, a piperidyl radical, a 3,5-dimethylpiperidyl radical, an indolinyl radical, a morpholinyl radical, a 2,6-dimethylmorpholinyl radical, a thiomorpholinyl radical, an azacycloheptyl radical, a phenothiazinyl radical, a phenoxazinyl radical, a 1,2,3,4-tetrahydroquinolyl radical, a 1,2,3,4-tetrahydroisoquinolyl radical, a phenazinyl radical, a carbazolyl radical, a 1,2,3,4-tetrahydrocarbazolyl radical or a 10,11-dihydrodibenz[b,f]azepinyl radical, preferably selected from hydrogen, a ($C_1$-$C_6$)-alkyl radical, a ($C_3$-$C_7$)-cycloalkyl radical, a ($C_1$-$C_6$)-thioalkyl radical, a ($C_1$-$C_6$)-alkoxy radical, a hydroxyl radical, a tert-butyldimethylsilyloxy radical, a tert-butyldiphenylsilyloxy radical, a trifluoromethyl radical, a phenyl radical, a 4-methoxyphenyl radical, a phenoxy radical, a 4-methoxyphenoxy radical, a benzyl radical, a 4-methoxybenzyl radical, a benzyloxy radical or a 4-methoxybenzyloxy radical.

5. An ophthalmic device comprising the photochromic fused naphthopyrans as claimed in claim 1, wherein the ophthalmic device is selected from the group consisting of: optical lenses, lenses for eyewear, corrective spectacles, driver's glasses, sunglasses, motorcycle googles, visors or protective helmets, car windows, building windows, protective shades, covers and roofs.

* * * * *